(12) United States Patent
Lindenbaum et al.

(10) Patent No.: US 7,115,127 B2
(45) Date of Patent: *Oct. 3, 2006

(54) METHODS AND APPARATUS FOR HEMOSTASIS FOLLOWING ARTERIAL CATHETERIZATION

(75) Inventors: Hayim Lindenbaum, Haifa (IL); Shimon Eckhouse, Haifa (IL)

(73) Assignee: CardioDex, Ltd., Tirat-Hacarmel (IL)

( * ) Notice: Subject to any disclaimer, the term of this patent is extended or adjusted under 35 U.S.C. 154(b) by 245 days.

This patent is subject to a terminal disclaimer.

(21) Appl. No.: 10/358,130

(22) Filed: Feb. 4, 2003

(65) Prior Publication Data

US 2004/0153054 A1 Aug. 5, 2004

(51) Int. Cl.
*A61B 18/04* (2006.01)

(52) U.S. Cl. .......................... 606/49; 128/898; 606/628; 606/40

(58) Field of Classification Search ............. 606/34–52; 128/898
See application file for complete search history.

(56) References Cited

U.S. PATENT DOCUMENTS

| 1,881,250 A | | 10/1932 | Tomlinson | |
|---|---|---|---|---|
| 3,595,238 A | | 7/1971 | Gavrilov et al. | |
| 3,886,944 A | * | 6/1975 | Jamshidi | 606/30 |
| 4,202,337 A | | 5/1980 | Hren et al. | |
| 4,211,230 A | | 7/1980 | Woltosz | |
| 4,364,392 A | | 12/1982 | Strother et al. | 128/325 |
| 4,539,987 A | | 9/1985 | Nath et al. | |
| 4,744,364 A | | 5/1988 | Kensey | 128/334 |
| 4,836,204 A | | 6/1989 | Landymore et al. | 128/334 |
| 4,869,248 A | | 9/1989 | Narula | |

(Continued)

FOREIGN PATENT DOCUMENTS

| WO | WO 93/21844 | 11/1993 |
|---|---|---|
| WO | WO 94/24948 | 11/1994 |
| WO | WO 98/11830 | 3/1998 |
| WO | WO 00/02488 | 1/2000 |
| WO | WO 02/072188 | 9/2002 |
| WO | WO-04/069300 | 8/2004 |
| WO | WO 04/071612 | 8/2004 |

OTHER PUBLICATIONS

Overview of CompressAR. 2002.
Angio–Seal™. 2002.
The Prostar®, Perclose, Inc. 2002.
Silber, S. "Vascular Closure Devices for Immediate..", in Handbook of Coronary Stents, 3$^{rd}$ ed. (Martin Dunitz).
"About AVD," 2002, http://www.compressar.com/about/index.shtml.

*Primary Examiner*—Henry M. Johnson, III
(74) *Attorney, Agent, or Firm*—Patton Boggs LLP

(57) ABSTRACT

A method for accelerating hemostasis of an artery having a puncture after arterial catheterization, the catheterization using a catheter introducer, the method including the steps of inserting into an artery a catheter introducer prior to arterial catheterization, following arterial catheterization, introducing a hemostasis device into the catheter introducer, such that a forward end of the hemostasis device lies exterior of the artery adjacent a puncture in a wall of the artery, accelerating hemostasis by heating blood in the vicinity of the puncture, thereby shortening the time required for hemostasis and following hemostasis, removing the catheter introducer and hemostasis device from the patient. A method for monitoring the progress of hemostasis of an artery is also disclosed.

11 Claims, 4 Drawing Sheets

U.S. PATENT DOCUMENTS

| | | | |
|---|---|---|---|
| 4,929,246 A | | 5/1990 | Sinofsky |
| 5,103,804 A | | 4/1992 | Abele et al. |
| 5,122,137 A | | 6/1992 | Lennox |
| 5,211,624 A | | 5/1993 | Cinberg et al. |
| 5,217,024 A | | 6/1993 | Dorsey et al. ............... 128/758 |
| 5,342,393 A | * | 8/1994 | Stack ......................... 606/213 |
| 5,349,166 A | * | 9/1994 | Taylor ........................ 219/643 |
| 5,370,660 A | | 12/1994 | Weinstein et al. .......... 606/215 |
| 5,383,896 A | | 1/1995 | Gershony et al. |
| 5,413,571 A | | 5/1995 | Katsaros et al. ............ 606/213 |
| 5,415,657 A | | 5/1995 | Taymor-Luria |
| 5,419,195 A | | 5/1995 | Quinn |
| 5,419,765 A | | 5/1995 | Weldon et al. ................ 604/96 |
| 5,458,573 A | | 10/1995 | Summers .................... 604/101 |
| 5,486,195 A | | 1/1996 | Myers et al. ............... 606/213 |
| 5,507,744 A | | 4/1996 | Tay et al. |
| 5,540,715 A | | 7/1996 | Katsaros et al. ............ 606/213 |
| 5,626,601 A | | 5/1997 | Gershony et al. ........... 506/175 |
| 5,645,566 A | | 7/1997 | Brenneman et al. ........ 606/213 |
| 5,700,277 A | | 12/1997 | Nash et al. .................. 606/213 |
| 5,716,375 A | | 2/1998 | Fowler |
| RE35,755 E | | 3/1998 | Qian |
| 5,725,551 A | | 3/1998 | Myers et al. ............... 606/213 |
| 5,728,133 A | | 3/1998 | Kontos |
| 5,728,134 A | | 3/1998 | Barak .......................... 606/214 |
| 5,782,860 A | | 7/1998 | Epstein et al. |
| 5,810,810 A | | 9/1998 | Tay et al. |
| 5,853,421 A | | 12/1998 | Leschinsky et al. ........ 606/213 |
| 5,868,778 A | | 2/1999 | Gershony et al. |
| 5,879,499 A | | 3/1999 | Corvi ......................... 156/175 |
| 5,891,138 A | | 4/1999 | Tu et al. |
| 5,895,386 A | | 4/1999 | Odell et al. |
| 5,922,009 A | | 7/1999 | Epstein et al. |
| 5,928,266 A | | 7/1999 | Kontos ....................... 606/213 |
| 5,941,897 A | | 8/1999 | Myers |
| 6,022,336 A | | 2/2000 | Zadno-Azizi et al. ......... 604/96 |
| 6,033,398 A | | 3/2000 | Farley et al. |
| 6,033,401 A | * | 3/2000 | Edwards et al. .............. 606/41 |
| 6,048,358 A | | 4/2000 | Barak .......................... 606/213 |
| 6,056,768 A | | 5/2000 | Cates et al. |
| 6,063,085 A | | 5/2000 | Tay et al. |
| 6,071,277 A | | 6/2000 | Farley et al. |
| 6,113,598 A | * | 9/2000 | Baker .......................... 606/51 |
| 6,126,635 A | | 10/2000 | Simpson et al. ............ 604/101 |
| 6,142,994 A | | 11/2000 | Swanson et al. |
| 6,152,920 A | | 11/2000 | Thompson et al. |
| 6,179,832 B1 | | 1/2001 | Jones et al. |
| 6,228,082 B1 | | 5/2001 | Baker et al. |
| 6,235,027 B1 | * | 5/2001 | Herzon ........................ 606/51 |
| 6,322,559 B1 | | 11/2001 | Daulton et al. |
| 6,352,533 B1 | | 3/2002 | Ellman et al. |
| 6,398,780 B1 | | 6/2002 | Farley et al. |
| 6,398,782 B1 | | 6/2002 | Pecor et al. |
| 6,402,745 B1 | | 6/2002 | Wilk |
| 6,443,947 B1 | * | 9/2002 | Marko et al. .................. 606/28 |
| 6,450,989 B1 | | 9/2002 | Dubrul et al. |
| 6,451,007 B1 | | 9/2002 | Koop et al. |
| 6,468,272 B1 | | 10/2002 | Koblish et al. |
| 6,529,756 B1 | | 3/2003 | Phan et al. |
| 6,533,778 B1 | * | 3/2003 | Herzon ......................... 606/28 |
| 6,551,313 B1 | | 4/2003 | Levin |
| 6,569,161 B1 | | 5/2003 | Zappala |
| 6,656,136 B1 | | 12/2003 | Weng et al. |
| 6,676,657 B1 | | 1/2004 | Wood |
| 6,676,685 B1 | | 1/2004 | Pedros et al. |
| 6,682,526 B1 | | 1/2004 | Jones et al. |
| 6,689,126 B1 | | 2/2004 | Farley et al. |
| 6,712,804 B1 | | 3/2004 | Roue et al. |
| 6,712,806 B1 | | 3/2004 | St. Germain et al. |
| 6,712,815 B1 | * | 3/2004 | Sampson et al. |
| 6,743,195 B1 | * | 6/2004 | Zucker |
| 6,768,086 B1 | * | 7/2004 | Sullivan et al. |
| 6,772,013 B1 | * | 8/2004 | Ingle et al. |
| 6,846,321 B1 | | 1/2005 | Zucker |
| 6,904,303 B1 | * | 6/2005 | Phan et al. |
| 2001/0003158 A1 | * | 6/2001 | Kensey et al. ............... 606/213 |
| 2001/0029373 A1 | | 10/2001 | Baker et al. |
| 2002/0072761 A1 | | 6/2002 | Abrams et al. |
| 2002/0156495 A1 | | 10/2002 | Brenneman et al. |
| 2002/0193808 A1 | | 12/2002 | Belef et al. |
| 2003/0055454 A1 | | 3/2003 | Zucker |
| 2003/0093116 A1 | | 5/2003 | Nowakowski |
| 2003/0109869 A1 | | 6/2003 | Shadduck |
| 2003/0120256 A1 | | 6/2003 | Lary et al. |
| 2003/0125766 A1 | | 7/2003 | Ding |
| 2003/0199863 A1 | | 10/2003 | Swanson et al. |
| 2003/0236518 A1 | | 12/2003 | Marchitto et al. |
| 2004/0010298 A1 | | 1/2004 | Altshuler et al. |
| 2004/0092913 A1 | | 5/2004 | Hennings et al. |
| 2004/0153054 A1 | | 8/2004 | Lindenbaum et al. |
| 2004/0153060 A1 | | 8/2004 | Lindenbaum et al. |
| 2004/0199155 A1 | | 10/2004 | Mollenaver |
| 2004/0249342 A1 | | 12/2004 | Khosravi et al. |

* cited by examiner

METHODS AND APPARATUS FOR HEMOSTASIS FOLLOWING ARTERIAL CATHETERIZATION

FIELD OF THE INVENTION

The present invention relates to methods and apparatus for hemostasis following arterial catheterization.

BACKGROUND OF THE INVENTION

Various techniques are known for arterial catheterization. Following arterial catheterization, it is necessary to promote hemostasis quickly and without undue hardship for the patient.

Applicant's U.S. Pat. Nos. 5,728,134 and 6,048,358, and published PCT Applications WO 98/11830 and WO 00/02488 describe methods and apparatus for hemostasis which greatly simplify hemostasis and thus greatly reduce patient discomfort following arterial catheterization. These patent documents, the disclosures of which are hereby incorporated by reference, and the prior art referenced therein are considered to represent the state of the art.

SUMMARY OF THE INVENTION

The present invention seeks to provide improved apparatus and techniques for measuring the progress of and accelerating hemostasis.

There is thus provided in accordance with a preferred embodiment of the present invention a method for monitoring the progress of hemostasis of an artery having a puncture after arterial catheterization, the catheterization using a catheter introducer, the method including the steps of inserting into an artery a catheter introducer prior to arterial catheterization, following arterial catheterization, introducing a hemostasis device into the catheter introducer, such that a forward end of the hemostasis device lies exterior of the artery adjacent a puncture in a wall of the artery, during hemostasis, measuring the heat conductivity of blood in the vicinity of the puncture, thereby to provide an output indication of the progress of hemostasis and following hemostasis, removing the catheter introducer and the hemostasis device from the patient.

Preferably, the method also includes inflating a balloon attached to the catheter introducer to block the puncture, prior to the introducing a hemostasis device. Additionally, the removing the catheter introducer also includes deflating the balloon prior to removing the catheter introducer.

There is also provided in accordance with another preferred embodiment of the present invention a method for accelerating hemostasis of an artery having a puncture after arterial catheterization, the catheterization using a catheter introducer, the method including the steps of inserting into an artery a catheter introducer prior to arterial catheterization, following arterial catheterization, introducing a hemostasis device into the catheter introducer, such that a forward end of the hemostasis device lies exterior of the artery adjacent a puncture in a wall of the artery, accelerating hemostasis by heating blood in the vicinity of the puncture, thereby shortening the time required for hemostasis and following hemostasis, removing the catheter introducer and hemostasis device from the patient.

In accordance with another preferred embodiment of the present invention the method also includes inflating a balloon attached to the catheter introducer to block the puncture, prior to the introducing a hemostasis device. Additionally, the removing the catheter introducer also includes deflating the balloon prior to removing the catheter introducer.

Alternatively or additionally, the method also includes measuring the heat conductivity of blood in the vicinity of the puncture during hemostasis, thereby to provide an output indication of the progress of hemostasis.

There is further provided in accordance with still another preferred embodiment of the present invention a hemostasis device including a resistance element, disposed at a forward end of the hemostasis device, a resistance sensor and a resistance indicator, operative to provide an indication of the resistance at the resistance sensor.

In accordance with another preferred embodiment of the present invention, the hemostasis device also includes a power supply serially connected to the resistance element, the resistance sensor and the resistance indicator. Preferably, the power supply is operative to supply a high level current to the resistance element. Alternatively, the power supply is operative to supply a low level current to the resistance sensor.

BRIEF DESCRIPTION OF THE DRAWINGS

The present invention will be understood and appreciated more fully from the following detailed description taken in conjunction with the drawings in which.

DETAILED DESCRIPTION OF A PREFERRED EMBODIMENT

Figure 1A:
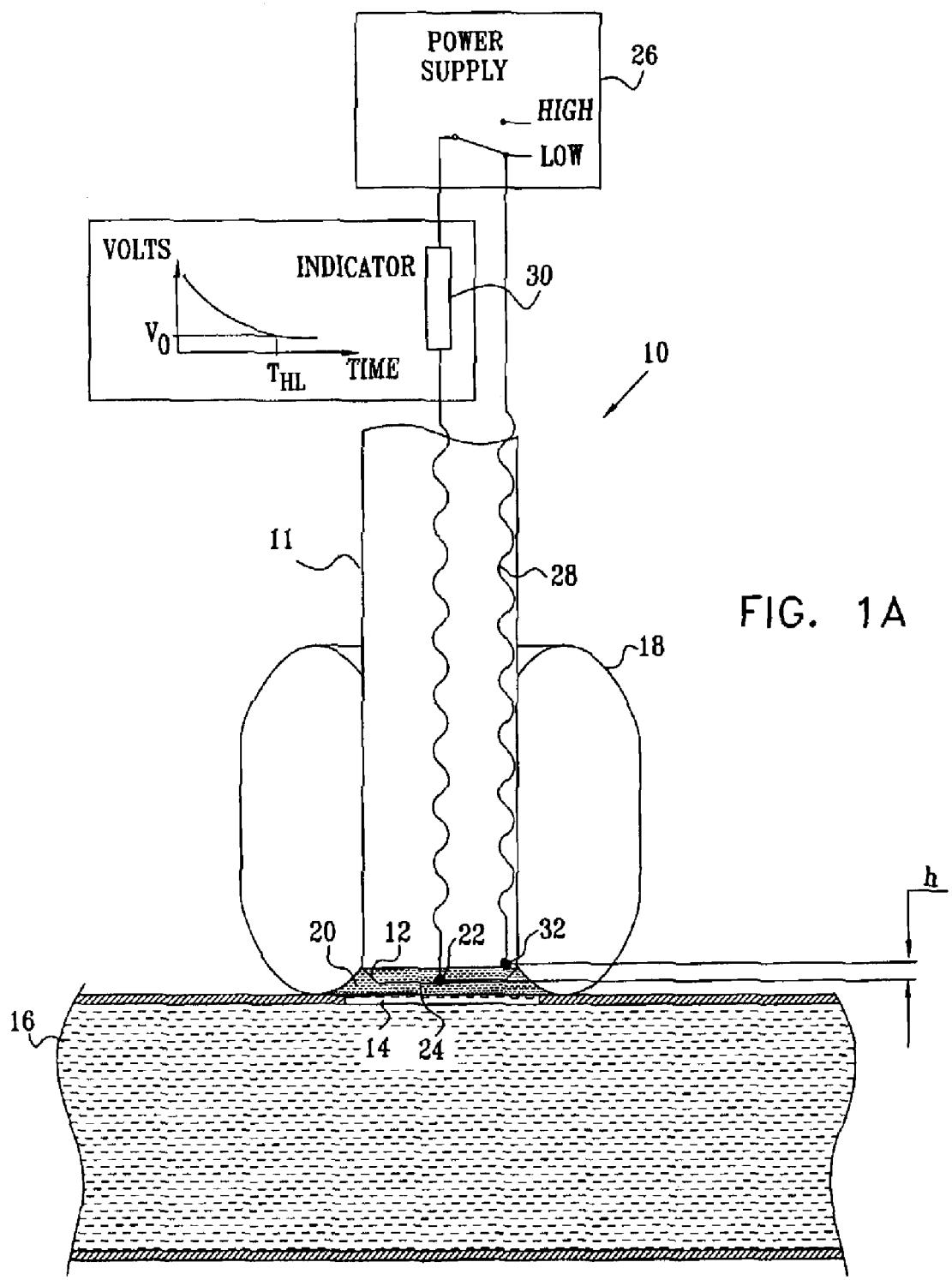
FIGS. 1A and 1B are simplified pictorial illustrations of respective first and second modes of operation of a hemostasis device constructed and operative in accordance with a preferred embodiment of the present invention.
Figure 1B:
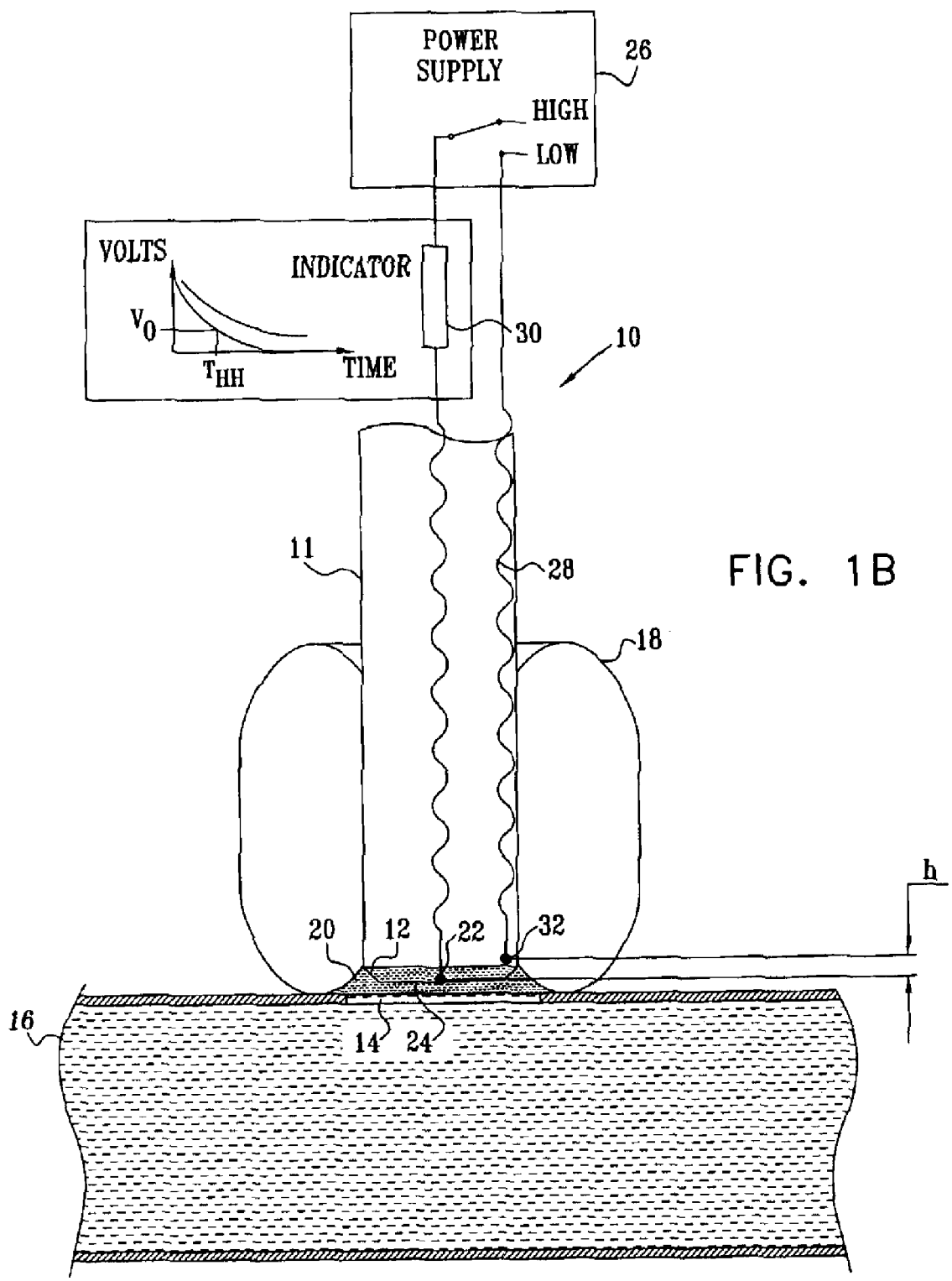

Reference is now made to FIGS. 1A and 1B, which are simplified pictorial illustrations of a preferred embodiment of a hemostasis device in respective first and second modes of operation.

As seen in FIG. 1A, a hemostasis device 10 is inserted into a catheter introducer 11, following arterial catheterization and withdrawal of a catheter (not shown), such that a forward end 12 of the hemostasis device 10 lies adjacent to and outside a puncture 14 in an artery 16. At least one external balloon 18 is preferably disposed adjacent catheter introducer 11 and is shown in an inflated orientation, wherein the balloon 18 forms a skirt surrounding and sealing puncture 14 from the tissue external thereto. At this stage blood normally fills artery 16 as well as puncture 14, as well as the annular volume 20 surrounded by balloon 18 adjacent puncture 14 and forward end 12.

In accordance with another preferred embodiment of the present invention, the at least one balloon 18 need not be provided.

In accordance with a preferred embodiment of the present invention, a resistance element 22 is disposed at a forward edge 24 of the forward end 12, and is coupled in series with an external power supply 26 via conductors 28, which typically extend along the length of the hemostasis device 10. Preferably, the series connection includes a resistance indicator 30, which provides an indication of the resistance at a resistance sensor 32.

As seen in FIG. 1A, a low level current, typically less than 0.1 ampere, is provided by external power supply 26 to enable the resistance indicator 30 to monitor the progress of hemostasis, to allow for timely removal of catheter introducer 11 and hemostasis device 10 from the patient.

It is appreciated that the heat conductivity of the blood in liquid form is measurably different from that of a blood clot formed during hemostasis, as will be described hereinbelow with reference to FIGS. 3A and 3B.

FIG. 1B illustrates the hemostasis device of FIG. 1A in a second preferred mode of operation. As shown in FIG. 1B, a high level electrical current, typically greater than 0.1 ampere, is supplied via the external power supply 26 to resistance element 22. The provision of this current causes heating of the blood adjacent to the resistance element 22 and provides for accelerated hemostasis. The provision of resistance indicator 30, connected to resistance sensor 32, enables the monitoring of the progress of the accelerated hemostasis, to allow for regulation of the current provided to resistance element 22 over time, and to allow timely removal of catheter introducer 11 and hemostasis device 10 from the patient.

It is appreciated that the heat conductivity of the blood in liquid form is measurably different from that of a blood clot formed during hemostasis, as will be described hereinbelow with reference to FIGS. 3A and 3B.

Figure 2:
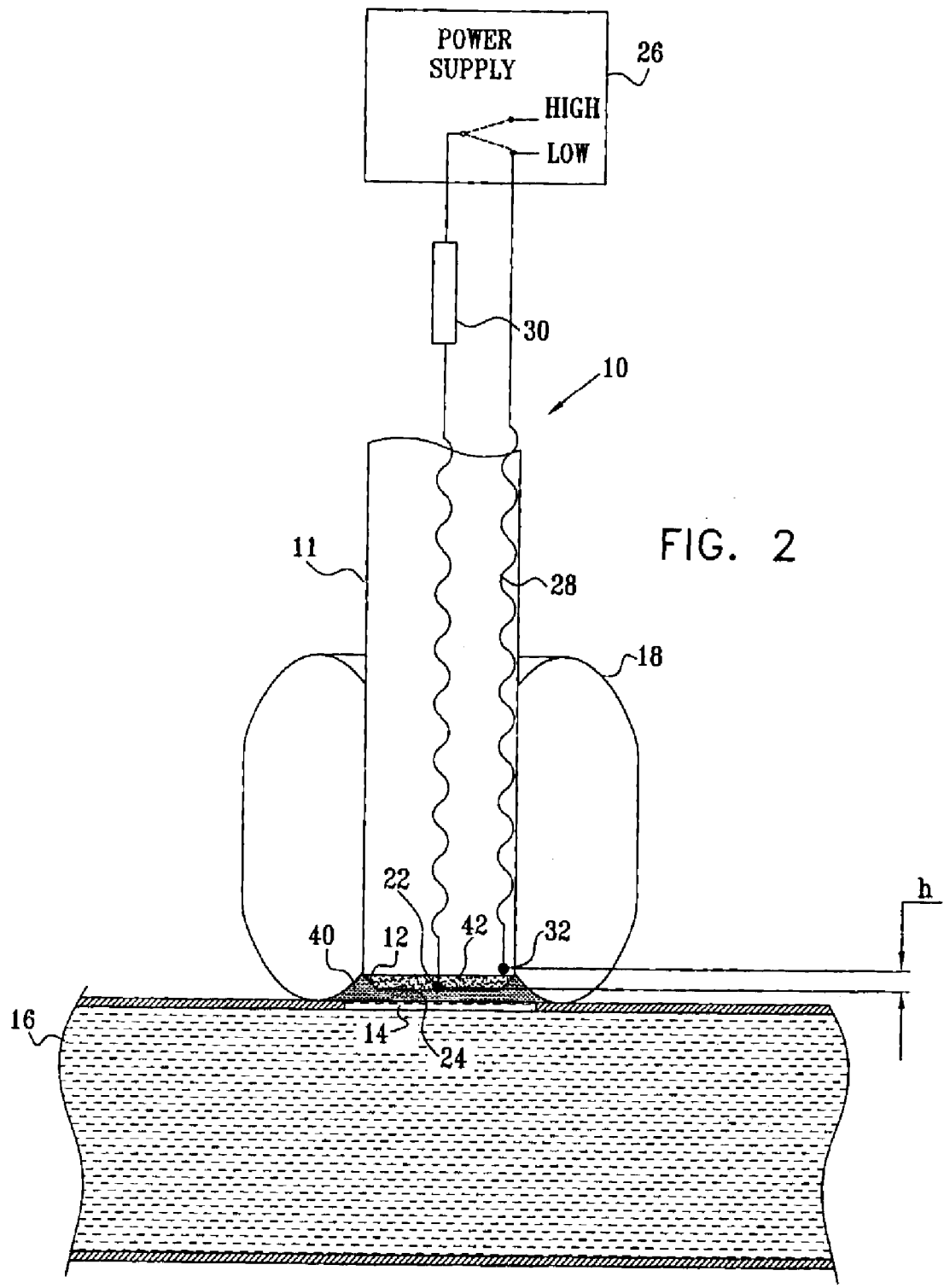
FIG. 2 is a simplified pictorial illustration of the hemostasis device of FIGS. 1A and 1B during hemostasis.

Reference is now made to FIG. 2, which is a simplified pictorial illustration of hemostasis device 10 of FIGS. 1A and 1B during hemostasis.

FIG. 2 shows the hemostasis device 10 of FIGS. 1A and 1B and illustrates the different heat conductivity of the blood during the various stages of hemostasis. As seen in FIG. 2, the blood flowing through the artery 16 and adjacent the puncture 14 in the artery is in liquid form, where its heat conductivity is greater than that of the blood 40 which has begun to coagulate. Blood 40 is in a viscous form, which has a heat conductivity greater than that of the blood 42, which has already begun to solidify into a blood clot. Resistance sensor 32 is thus able to measure the process of coagulation by measuring the heat conductivity of the adjacent blood.

Figure 3A:
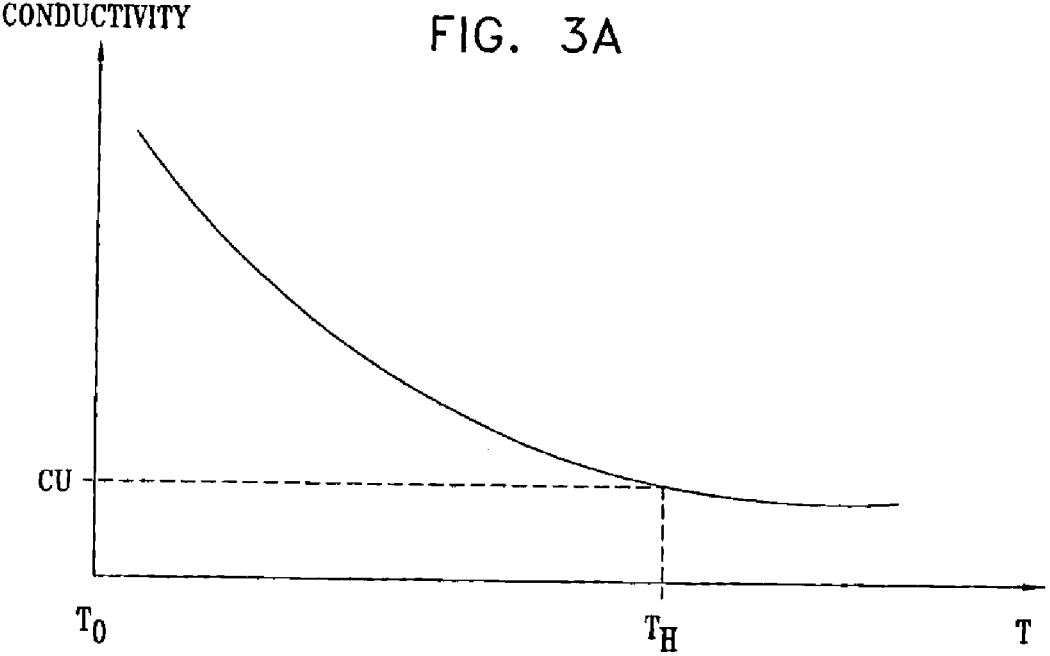
FIGS. 3A and 3B are graphs illustrating the typical conductivity levels measured by the hemostasis device when used in the operating modes shown in FIGS. 1A and 1B, respectively.
Figure 3B:
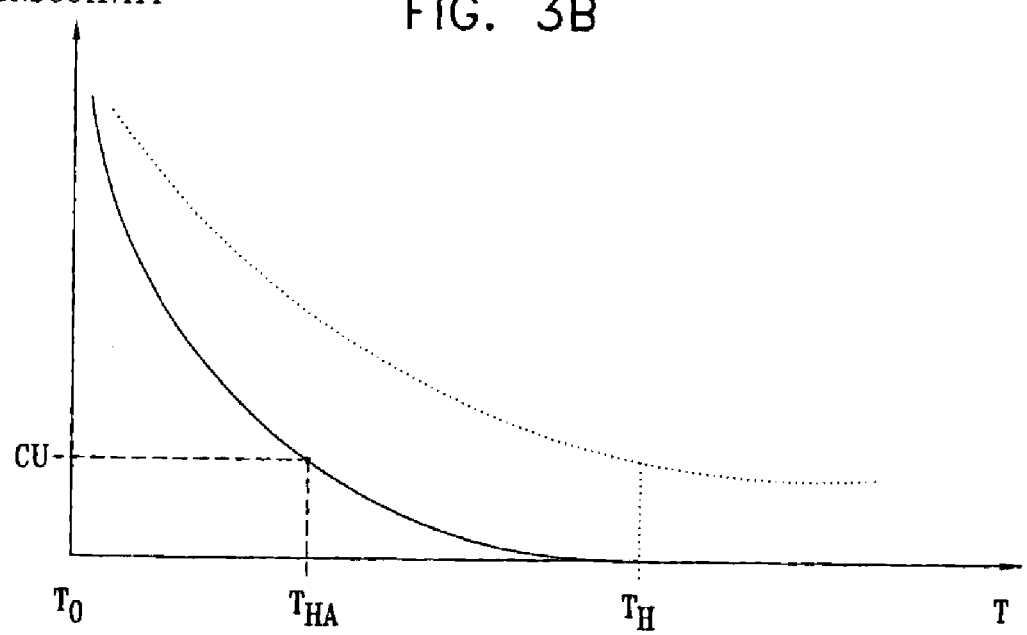

Reference is now made to FIGS. 3A and 3B, which are graphs illustrating the typical conductivity levels measured by the catheter introducer assembly when used in the operating modes shown in FIGS. 1A and 1B, respectively.

FIG. 3A shows the heat conductivity of the blood over time, in the mode of operation illustrated in FIG. 1A, where the blood is in a liquid form at time $T_0$, with relatively high heat conductivity, where the heat conductivity decreases gradually over time as the blood forms a clot at time $T_H$.

FIG. 3B shows the heat conductivity of the blood over time, in the mode of operation illustrated in FIG. 1B, where the blood is heated to accelerate clotting. As seen in FIG. 3B, the heat conductivity begins at time $T_0$ in a liquid form with relatively high heat conductivity, which decreases rapidly as the blood is heated and the clotting occurs at an accelerated rate. FIG. 3B also shows the heat conductivity curve over time shown in FIG. 3A, which clearly illustrates the accelerated hemostasis described in reference to FIG. 1B hereinabove, where $T_{HA}$ is the accelerated hemostasis time and $T_H$ is the non-accelerated hemostasis time.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specification and which are not in the prior art.

What is claimed is:

1. A method for monitoring the progress of hemostasis of an artery having a puncture after arterial catheterization, said catheterization using a catheter introducer, the method comprising the steps of:
   inserting into an artery a catheter introducer prior to arterial catheterization;
   following arterial catheterization, introducing a hemostasis device into said catheter introducer, such that a forward end of said hemostasis device lies exterior of the artery adjacent a puncture in a wall of the artery;
   during hemostasis, measuring the beat conductivity of blood in the vicinity of said puncture, thereby to provide an output indication of the progress of hemostasis; and
   following hemostasis, removing said catheter introducer and said hemostasis device from the patient.

2. A method for monitoring the progress of hemostasis according to claim 1 and also comprising inflating a balloon attached to said catheter introducer to block said puncture, prior to said introducing a hemostasis device.

3. A method for monitoring the progress of hemostasis according to claim 2 and wherein said removing said catheter introducer also comprises deflating said balloon prior to removing said catheter introducer.

4. A method for accelerating hemostasis of an artery having a puncture after arterial catheterization, said catheterization using a catheter introducer, the method comprising the steps of:
   inserting into an artery a catheter introducer prior to arterial catheterization;
   following arterial catheterization, introducing a hemostasis device into said catheter introducer, such that a forward end of said hemostasis device lies exterior of the artery adjacent a puncture in a wall of the artery;
   accelerating hemostasis by heating blood in the vicinity of said puncture, thereby shortening the time required for hemostasis; and
   following hemostasis, removing said catheter introducer and hemostasis device from the patient.

5. A method for accelerating hemostasis of an artery according to claim 4 and also comprising inflating a balloon attached to said catheter introducer to block said puncture, prior to said introducing a hemostasis device.

6. A method for accelerating hemostasis of an artery according to claim 5 and wherein said removing said catheter introducer also comprises deflating said balloon prior to removing said catheter introducer.

7. A method according to claim 4 and also comprising measuring the heat conductivity of blood in the vicinity of said puncture during hemostasis, thereby to provide an output indication of the progress of hemostasis.

8. Hemostasis apparatus comprising:
   an elongate element;
   at least one inflatable balloon disposed adjacent a forward end of said elongate element and being adapted to form a skirt surrounding and sealing a puncture in an artery;
   a resistance element, disposed at a forward edge of said forward end and being operative as a resistance heater adapted to heat blood adjacent said resistance element and as a resistance sensor adapted for sensing the resistance of said blood; and a resistance indicator, operative to provide an indication of the resistance at said resistance sensor, and thus being adapted to monitor the progress of hemostasis.

9. A hemostasis device according to claim 8 and also comprising a power supply serially connected to said resistance element, and said resistance indicator.

10. A hemostasis device according to claim 9 and wherein said power supply is operative to supply a high level current to said resistance element.

11. A hemostasis device according to claim 9 and wherein said power supply is operative to supply a low level current to said resistance element.

* * * * *